(12) United States Patent
Barker

(10) Patent No.: US 9,004,072 B2
(45) Date of Patent: Apr. 14, 2015

(54) CANNULA SUPPORT ASSEMBLY

(71) Applicant: Norman D. Barker, Eddyville, OR (US)

(72) Inventor: Norman D. Barker, Eddyville, OR (US)

( * ) Notice: Subject to any disclaimer, the term of this patent is extended or adjusted under 35 U.S.C. 154(b) by 123 days.

(21) Appl. No.: 13/754,755

(22) Filed: Jan. 30, 2013

(65) Prior Publication Data

US 2014/0209099 A1  Jul. 31, 2014

(51) Int. Cl.
*A61M 11/00* (2006.01)
*A61M 16/06* (2006.01)

(52) U.S. Cl.
CPC ....... *A61M 16/0683* (2013.01); *A61M 16/0666* (2013.01); *A61M 2202/0208* (2013.01); *A61M 16/0672* (2014.02)

(58) Field of Classification Search
CPC .............. A61M 15/08; A61M 15/085; A61M 16/0666; A61M 16/0672; A61M 16/0683; A61M 25/02; G02C 11/00; G02C 11/08
USPC ............. 128/200.28, 201.12, 201.15, 201.22, 128/201.24, 202.13, 206.27, 207.18; 351/41, 51–52, 155, 158; D16/300, D16/309, 330
See application file for complete search history.

(56) References Cited

U.S. PATENT DOCUMENTS

| | | | | |
|---|---|---|---|---|
| 2,245,969 A * | 6/1941 | Francisco et al. | ........ | 128/207.18 |
| 3,209,755 A * | 10/1965 | McCarthy et al. | ............ | 604/174 |
| 4,454,880 A * | 6/1984 | Muto et al. | ............... | 128/205.25 |
| 4,465,067 A * | 8/1984 | Koch et al. | ............... | 128/207.18 |
| 4,708,446 A * | 11/1987 | Timmons et al. | ............. | 351/158 |
| 4,995,384 A | 2/1991 | Keeling | | |
| 5,117,818 A * | 6/1992 | Palfy | ........................ | 128/204.11 |
| 5,193,534 A * | 3/1993 | Peppler | .................... | 128/207.18 |
| 5,438,979 A | 8/1995 | Johnson, Jr. et al. | | |
| 5,533,506 A * | 7/1996 | Wood | ........................ | 128/207.18 |
| 6,684,883 B1 | 2/2004 | Burns | | |
| 7,156,097 B2 | 1/2007 | Cardoso | | |
| 8,336,551 B1 | 12/2012 | Preston et al. | | |
| 2010/0000534 A1* | 1/2010 | Kooij et al. | ............... | 128/204.18 |
| 2013/0255683 A2* | 10/2013 | Kapust et al. | ............ | 128/204.23 |

* cited by examiner

*Primary Examiner* — Steven Douglas

(57) ABSTRACT

A cannula support assembly capable of supporting a nasal cannula that delivers oxygen or other gas or gas mixtures to a user is disclosed. The assembly has a plurality of retention clips into which cannula tubes are inserted and retained in a manner so as not to interfere or cause discomfort to a user. The front support assembly housing has a left and a right depression that lowers housing elements well below the line-of-sight of the user so that his or her vision is not impaired when using the assembly. The depressions also allow for the user to wear eyeglasses in conjunction with using the assembly.

20 Claims, 4 Drawing Sheets

CANNULA SUPPORT ASSEMBLY

CROSS-REFERENCES TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

SEQUENCE LISTING

Not Applicable

BACKGROUND OF THE INVENTION

1. Field of the Invention

The present invention relates to devices used in securing medical equipment to the head and face, and more specifically, to devices for securing nasal cannulas.

2. Description of the Related Art

In the troposphere, atmospheric gas used in breathing consists of approximately seventy-eight percent nitrogen, twenty-one percent oxygen, and many other trace elements such as carbon dioxide and argon. Of these gases, oxygen, in the elemental form of dioxygen, is the most abundantly used atmospheric gas in the cellular respiration required for homeostasis in living vertebrates. Without oxygen, cellular respiration becomes anaerobic, and can only function for a brief moment before cell damage or cell death occurs.

It is well known within the medical and sports professions that supplemental oxygen can ease labored breathing and offer relief to individuals whom are unable to extract sufficient oxygen from normal atmospheric inhalation by supplying a source of pure oxygen in and around the airways. This oxygen can originate from a plurality of sources such as, but not limited to, rebreathers, tanks, or regulators.

One method of supplying oxygen to an individual suffering from general hypoxia is to apply a mask to the face surrounding the nose and mouth that is secured using an adjustable or elastic strap encompassing the head or neck. The mask possesses an attached cannula providing free-flowing oxygen to the mask opening. This modality of oxygen delivery works sufficiently during short-term use, but is cumbersome to wear and does not allow the user to easily eat, speak, or otherwise use the mouth unless the mask is removed, which disrupts the flow of oxygen.

Within the related art came the need for an open-face cannula system to allow the user the use of their mouth, and as such, applying the flow of oxygen to the nasal passage became the preferred method of administration.

A simple cannula hose was developed with a small centrally-located reservoir that entered the nostrils and supplied flowing oxygen without impeding upon use of the mouth. The cannula was held in place by placing the reservoir within the nostrils then wrapping the cannula hose posteriorly behind both ears, thus applying rearward pressure against the face. This eventually became inconvenient to the user, as the pulling forces placed upon the ears became uncomfortable. The placement of the hoses also placed undue pressure upon the areas normally reserved for the arms of eyeglasses.

In an effort to relieve pressure on the ears, another device within the related art presented a modified eyeglass frame which transmitted oxygen via two small tubes running through the arms of the unit, down the nose frame, and exiting the unit just above the nostrils. The exited tubes then hooked into the nasal passageway and supplied the user with the preferred gasses. This eliminated pressure upon the ears, but limited the ability of the user to wear eyeglasses of their preference. Another inconvenience was the non-modular construction of the device. If any part of the device should become compromised from normal use or inflicted damage, the entire unit must be replaced at a significant cost to the end user.

In an effort to simplify the securement of nasal cannulas, practitioners began using single-sided adhesive strips to trap the cannula against the face. Unfortunately, this simple, but effective method often leaves adhesive residues on the skin, creating unsightly dermal irritation and or dark blotches that require solvents to remove.

Another modality within the related art of securing a nasal cannula are small clips for encompassing and subsequently affixing the cannula to headwear such as hats, or glasses in an effort to relieve pressure from the posterior ear. This required the user to continuously wear some form of headdress for the clips to attach to, which is not convenient, and occasionally inappropriate such as at certain ceremonies.

It could be said within the related art there are many reasonable and purposefully specific cannula securement devices but none offer the security attachment, comfort, reliability, ease of replacement, and versatility required by those using a nasal cannula for extended periods. The present invention addresses these needs by providing an appropriately over-sized eyeglass-like frame from which a standard nasal cannula assembly removably attaches. This spreads the force of the cannula across several points on the head, lessening the perceived force on any specific area.

BRIEF SUMMARY OF THE INVENTION

It is therefore an object of the present invention to provide a nasal cannula support assembly that securely supports a nasal cannula.

It is another object of the present invention to provide a nasal cannula support assembly that allows a user to wear eyeglasses while using the support assembly.

It is yet another object of the present invention to provide a nasal cannula support assembly that is comfortable to wear and does not cause rubbing or irritation to a user.

It is yet another object of the present invention to provide a nasal cannula support assembly that allows a user to quickly and easily install or remove a nasal cannula.

It is yet another object of the present invention to provide a nasal cannula support assembly that secures behind a user's ears and is not prone to dislodgement or accidental removal.

It is yet another object of the present invention to provide a nasal cannula support assembly that is lightweight, cost-efficient to manufacture, and easy to use.

It is yet another object of the present invention to provide a nasal cannula support assembly that does not block the vision of a user and is not bulky or otherwise obstructive.

In accordance with the objects of the invention described above, one exemplary embodiment of the present invention provides a nasal cannula support assembly with a frame and support arms to which a nasal cannula is attached by way of a plurality of retention clips. One of the primary disadvantages of the prior art is the tendency for nasal cannulas to become dislodged or fall off a user's face. The present invention overcomes that disadvantage by providing an apparatus for securely holding a nasal cannula in place on a user's face. The frame and support arms may be designed in such a manner as to allow a user to wear prescriptive or non-prescriptive eyeglasses while simultaneously wearing the nasal cannula support assembly. The support arms may act in a manner similar to the arms of traditional eyeglasses and be curved at the posterior portion so that they grip or hold on to the user's ears. The retention clips may be located along the bottom portion of the support assembly and may be shaped so that the tubing of a nasal cannula can be easily snapped into each retention clip. The shape of the retention clips may provide sufficient mechanical friction as to prevent the cannula tubing from accidental removal while not exerting enough pressure on the tubing to impede the flow of gasses.

The preceding brief description is intended to merely outline some objects and advantages of the present invention. The following disclosure will set forth other objects and advantages of the present invention along with novel features that distinguish the present invention from the prior art. It is to be understood that the following disclosure is by no means intended to limit the scope of the present invention or any of its embodiments. It is also to be understood that the accompanying illustrations are presented for descriptive purposes only and similarly are not intended to limit the scope of present invention or any of its embodiments. The following disclosure and accompanying illustrations may describe various features of novelty that characterize the invention. The invention does not reside any particular feature when taken in the singular, but in the combination of features as described herein.

BRIEF DESCRIPTION OF THE SEVERAL VIEWS OF THE IMAGE(S)

DETAILED DESCRIPTION OF THE INVENTION

Figure 1:
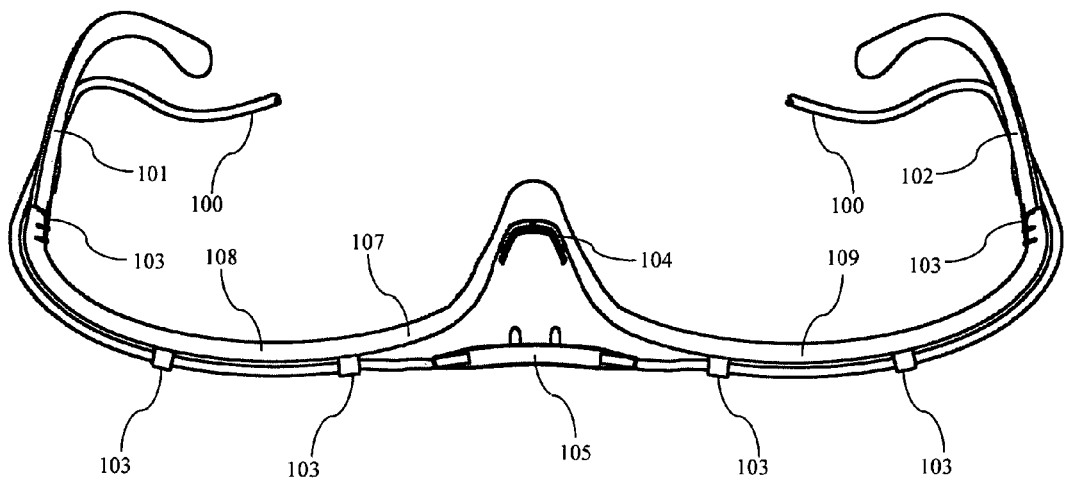
FIG. 1 is a top view of a nasal cannula support assembly as according to one embodiment of the present invention.

In the following detailed description, reference is made to the accompanying images that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. Furthermore, a particular feature, structure, or characteristic described herein in connection with one embodiment may be implemented within other embodiments without departing from the scope of the invention. In addition, it is to be understood that the location or arrangement of individual elements within each disclosed embodiment may be modified without departing from the scope of the invention. The following detailed description is, therefore, not to be taken in a limiting sense, and the scope of the present invention is defined only by appended claims, appropriately interpreted, along with the full range of equivalents to which the claims are entitled.

The word "exemplary" is used herein to mean "serving as an example, instance, or illustration." Any embodiment described herein as "exemplary" is not necessarily to be construed as preferred or advantageous over other embodiments. Likewise, the terms "embodiment(s) of the invention", "alternative embodiment(s)", and "exemplary embodiment(s)" do not require that all embodiments of the method, system, and apparatus include the discussed feature, advantage or mode of operation. The following description of the preferred embodiment is merely exemplary in nature and is in no way intended to limit the invention, its application, or use.

For the purpose of clarity, all like elements will have the same designations in each of the images. The terms "cannula support assembly", "assembly", "present invention", and "invention" may be used interchangeably. In addition to the functions, features, components, and abilities of the apparatus already discussed in this specification, the cannula support assembly may also have, but not be limited to, the following features contained within the description set forth herein.

Several preferred embodiments of the cannula support assembly are discussed in this section. However, the invention is not limited to these embodiments. A cannula support assembly is any device with a frame and support arms to which a nasal cannula is attached by way of a plurality of retention clips. The cannula support assembly is not limited in method of operation, dimensions, means for securing the cannula support assembly to the face of a user, or any other feature appropriate for inclusion as part of a cannula support assembly.

As set forth in this description and the attached images, an improved cannula support assembly has been developed that improves upon conventional cannula support devices. The various embodiments of the improved cannula support assembly described herein can be used in a wide variety of applications. For example, certain embodiments are particularly well-adapted for use with patients that wear eyeglasses. The improved cannula support assembly may fit onto a user's face while leaving sufficient clearance for a user to wear eyeglasses behind the support assembly. Other embodiments are particularly well-adapted for use with nasal cannulas that provide oxygen to a user. Even other embodiments are particularly well adapted for extended periods of comfortable use by providing three points of weight distribution; the left ear, the right ear, and the nose. The preceding exemplary uses are not intended to be limiting, but are merely illustrative for the possible uses of the cannula support assembly.

FIG. 1 illustrates a top view of a nasal cannula support assembly as according to one embodiment of the present invention. The assembly may comprise a right support arm (101), a left support arm (102), a plurality of retention clips (103), a nasal support (104), a front assembly piece (107), a right front assembly piece depression (108), and a left front assembly piece depression (109). The assembly may provide support for cannula tubes (100) by providing for the cannula tubes (100) to be inserted into the retention clips (103). The cannula tubes (100) may connect to a cannula junction with output nozzles (105) which, in turn, is inserted into a user's nostrils. The nasal support (104) may allow the assembly to rest on the bridge of a user's nose. The nasal support (104) may rest far enough down the bridge of a user's nose so as to permit eyeglasses to be worn at the same time as the assembly.

In one embodiment of the present invention, the nasal support may rest approximately midway along the bridge of the user's nose. The nasal support may not reside too high up on the bridge of a user's nose where it could potentially interfere with eyeglasses, or too far low on a user's nose where it may cause discomfort or be prone to slipping off. A user's vision may not be impaired when wearing the assembly because of left and right front assembly piece depressions (108, 109) formed in the front assembly housing (107) which may be located in front of a user's left and right eyes.

The right support arm (101), the left support arm (102), and the front assembly piece (107) may be considered, when taken together, as a framework for supporting a nasal cannula. The framework may be roughly similar in shape and function to the frame of sunglasses where right and left support arms provide securing means by wrapping partially around the ears of a user. The plurality of retention clips (103) and the nasal support (104) may attach to the underside of the framework for support and retention purposes. The right and left front assembly piece depressions (108, 109), may be molded into the framework and may lower the frame pieces below the line-of-sight of the user in front of their right and left eyes.

The left and right front assembly piece depressions (108, 109) may be located and shaped in a manner as not to impede the vision of the user. The left and right front assembly piece depressions (108, 109) may be sections of the front assembly piece that dip substantially below the line-of-sight of the user when the user is wearing the nasal cannula support assembly. The left and right front assembly piece depressions (108, 109) may be sufficiently spaced away from the eyes of the user so as to permit the user to wear prescription or non-prescription eyeglasses behind the front assembly housing (107).

Figure 2:
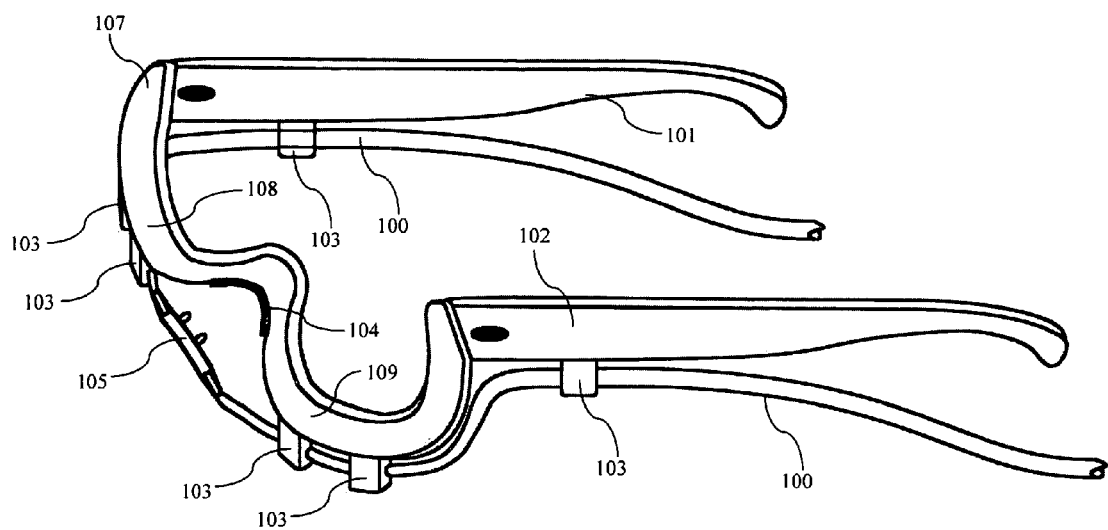
FIG. 2 is a perspective view of a nasal cannula support assembly as according to one embodiment of the present invention.

FIG. 2 illustrates a perspective view of a nasal cannula support assembly as according to one embodiment of the present invention. The right support arm (101) and left support arm (102) may be shaped with curved posterior portions designed to hook around a user's ears. The curved posterior portions may act as two support points that secure the nasal cannula support assembly to the user's face. The third contact point might be the nasal support (104) that may rest upon the bridge of the user's nose. It should be noted that in one preferred embodiment of the present invention, the optimal placement for the nasal support (104) could be midway along the bridge of a user's nose. By resting midway along the bridge of the user's nose, the nasal support (104) may be located so that the assembly does not interfere with eyeglasses worn by the user. Furthermore, by resting midway along the bridge of the user's nose, the nasal support may be located so that it does not easily become dislodged or fall from the user's face. The right and left support arms (101, 102) may have one or more retention clips (103) into which cannula tubes (100) may be inserted. The cannula tubes may also be inserted into retention clips (103) along the bottom of the front assembly piece (107). The retention clips (103) may be located on the right and left front assembly piece depressions (108, 109) so that the cannula tubes (100) are properly restrained and do not contact the user's face or interfere with the user's daily activities. The cannula tubes (100) may terminate in a cannula junction with output nozzles (105). The output nozzles may be inserted into the user's nostrils when the nasal cannula support assembly is in use.

Figure 3:
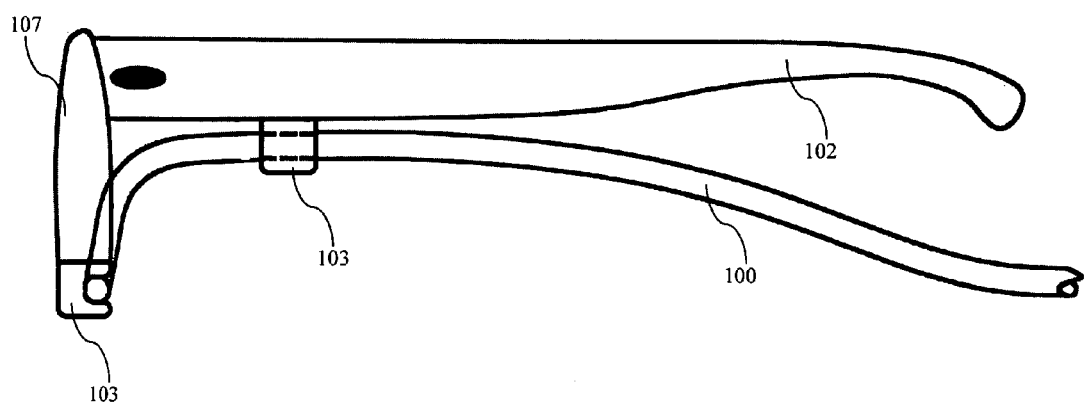
FIG. 3 is a side view of a nasal cannula support assembly as according to one embodiment of the present invention.

FIG. 3 illustrates a side view of a nasal cannula support assembly as according to one embodiment of the present invention. A cannula tube (100) may be connected to the left support arm (102) and to the front assembly piece (107) by way of retention clips (103). The retention clips (103) may be located on the underside of the left support arm (102) and front assembly piece (107) so that the cannula tube (100) is retained in a location that promotes user comfort and does not interfere with the user's vision or cause the user discomfort.

Figure 4:
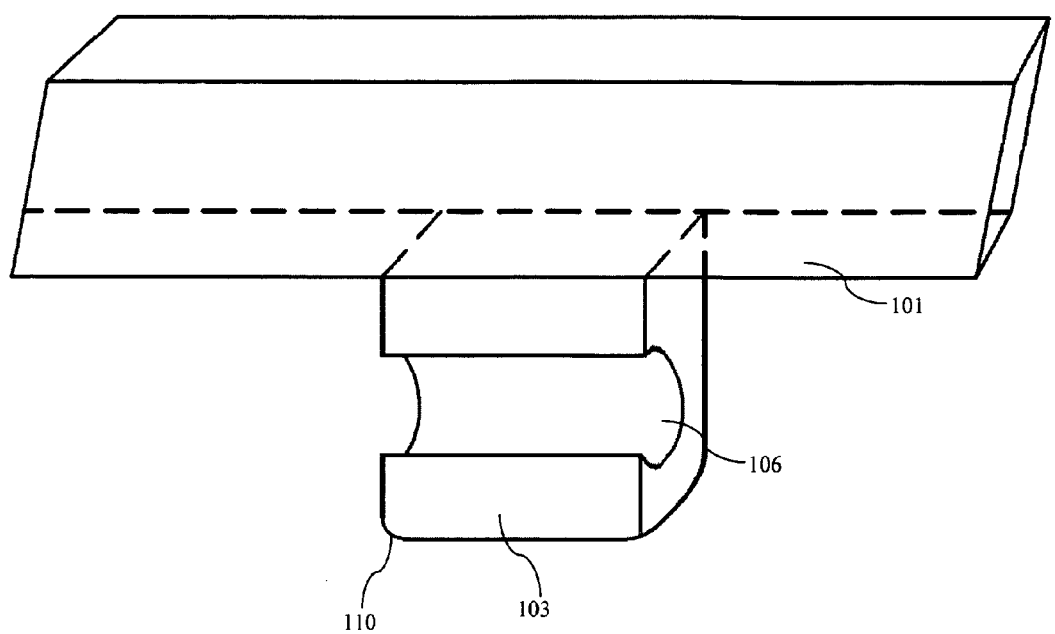
FIG. 4 is a retention clip attached to a nasal cannula support assembly as according to one embodiment of the present invention.

FIG. 4 illustrates a retention clip (103) attached to a nasal cannula support assembly as according to one embodiment of the present invention. The retention clip (103) may have an interior curvature (106) that is slightly smaller in diameter than that the cannula tube which fits into the retention clip (103). The smaller diameter of the retention clip's interior curvature (106) may compress the cannula tube when it is inserted into the retention clip (103) so that the cannula tube remains firmly affixed within the retention clip (103). By way of example, the exterior diameter of an oxygen cannula tube may be 0.125 inches. A retention clip (103) of the present invention designed to work with an oxygen cannula tube may have an in interior curvature (106) with a diameter of 0.122 inches. The difference between the diameters may provide a compressive force that keeps the oxygen cannula tube securely in place. However, the compression of any cannula tube inserted into a retention clip (103) caused by the differing diameters will not result in the flow of gas to stop or otherwise be impeded. The interior curvature (106) of the retention clip (103) may be roughly C-shaped so as to provide a lip or edge that retains inserted cannula tubes. Inserted cannula tubes may snap or clip into place when inserted into the retention clips (103). The retention clips may also have radiused edges (110) so that a user is not scratched or lacerated if the retention clip comes in contact with the user's skin. The retention clips (103) may be made out of plastic, metal, or any other material that is suitable for use as retention clips (103) of the present invention. The retention clips (103) may be located along the left and right support arms (102, 100: FIGS. 1, 2, 3) or the front assembly piece (107: FIGS. 1, 2, 3).

The present invention may be suitable to use with cannula tubes that carry supplemental oxygen to a user as part of oxygen therapy. The present invention may also be used as part of nasal high flow therapy where blends or air and oxygen are administered to the user. Furthermore, the present invention may be used to carry any gas mixture that is administered to a user by way of a nasal cannula device including, but not limited to, those gasses or gas mixtures that require respiratory gas humidification.

Although certain example methods, apparatus and articles of manufacture have been described herein, the scope of coverage of this patent is not limited thereto. On the contrary, this patent covers all methods, apparatus and articles of manufacture fairly falling within the scope of the invention either literally or under the doctrine of equivalents.

With respect to the above description then, it is to be realized that the optimum dimensional relationships for the parts of the cannula support assembly, to include variations in size, materials, shape, form, function and the manner of operation, assembly and use, are deemed readily apparent and obvious to one skilled in the art, and all equivalent relationships to those illustrated in the images and described in the specification are intended to be encompassed by the cannula support assembly.

Directional terms such as "front", "back", "in", "out", "downward", "upper", "lower", "top", "bottom", and the like may have been used in the description. These terms are applicable to the embodiments shown and described in conjunction with the images. These terms are merely used for the purpose of description in connection with the images and do not necessarily apply to the position in which the cannula support assembly may be used.

Therefore, the foregoing is considered as illustrative only of the principles of the cannula support assembly. Further, since numerous modifications and changes will readily occur to those skilled in the art, it is not desired to limit the cannula support assembly to the exact construction and operation shown and described, and accordingly, all suitable modifications and equivalents may be resorted to, falling within the scope of the cannula support assembly. While the above description describes various embodiments of the present invention, it will be clear that the present invention may be otherwise easily adapted to fit any configuration where a cannula support assembly is desired or required.

As various changes could be made in the above constructions without departing from the scope of the invention, it is intended that all matter contained in the above description or shown in the accompanying images shall be interpreted as illustrative and not in a limiting sense.

What is claimed is:

1. A cannula support assembly for use in supporting a nasal cannula comprising:
a right support arm with a curved posterior portion and a bottom side, a left support arm with a curved posterior portion and a bottom side, wherein the curved posterior portion of the right support arm wrap is adapted to wrap significantly around a right ear of a user and the curved posterior portion of the left support arm is adapted to wrap significantly around a left ear of the user, wherein the adaptation of the curved posterior portion of the right support arm and left support arm create a securing tension around the left and right ears of the user, a front assembly piece with a bottom side, a plurality of retention clips adapted to affix at least one cannula tube, the plurality of retention clips having corners, the cannula tube having an outer diameter, a nasal support adapted to rest upon the bridge of the user's nose when the cannula support assembly is in use, a right front assembly piece depression shaped so that the user's vision is not impaired when using the cannula support assembly, and a left front assembly piece depression shaped so that the user's vision is not impaired when using the cannula support assembly.

2. The apparatus of claim 1, wherein the plurality of retention clips are located along the bottom side of the right support arm, the bottom side of the left support arm, and the bottom side of the front assembly piece.

3. The apparatus of claim 1, wherein each of the plurality of retention clips an interior curvature, the interior curvature having an inner diameter.

4. The apparatus of claim 3, wherein the inner diameter of the interior curvature is less than the outer diameter of the affixed cannula tube.

5. The apparatus of claim 3, wherein at least one of the corners of the retention clips is radiused.

6. The apparatus of claim 1, wherein the posterior portions of the right support arm and the left support arm are adapted to pass over and partially around the user's ears when the cannula support assembly is worn by the user.

7. The apparatus of claim 1, wherein the right front assembly piece depression and the left front assembly piece depression are shaped to allow the user to wear prescription or non-prescription eyeglasses behind the cannula support assembly.

8. A method for providing support for a nasal cannula worn by a user comprising:
providing a nasal cannula support assembly with a plurality of retention clips adapted to affix at least one cannula tube through which gas flows, the cannula tube having an outer diameter, providing left and right depressions in a front piece of the nasal cannula support assembly that allows the user to wear prescription or non-prescription eyeglasses when using the nasal cannula support assembly, and providing right and left support arms adapted to secure the nasal cannula support assembly to the user's head by wrapping most of the way around a left and a right ear of the user to create tension around the rear portion of the user's ears.

9. The method of claim 8, wherein each of the plurality of retention clips has an interior curvature with an inner diameter less than the outer diameter of the cannula tube.

10. The method of claim 9, wherein the inner diameter of the interior curvatures of the plurality of retention clips is smaller than the outer diameter of the cannula tube and the cannula tube is compressively secured when inserted into the retention clips.

11. The method of claim 10, wherein the difference between the diameter of the interior curvatures of the plurality of retention clips and the outer diameter of the tubes of the nasal cannula do not impede the flow of gas within the tubes of the nasal cannula.

12. The method of claim 8, wherein the front piece of the nasal cannula support assembly further comprises a nasal support adapted to rests upon a bridge of the user's nose when the nasal cannula support assembly is worn by the user.

13. The method of claim 12, wherein the nasal support is located between the left and right depressions in the front piece of the nasal cannula support assembly.

14. An assembly comprising:
a framework for supporting a nasal cannula, wherein the framework consists of a front piece, left and right support arms adapted to secure the framework to a user's head by wrapping significantly around at least one ear of the user, and a bottom side; a plurality of retention clips adapted to affix at least one cannula tube having an outer diameter to the bottom side of the framework, the plurality of retention clips each having an interior curvature, the interior curvatures having a diameter; a nasal support attached to the front piece of the framework adapted to rest on a bridge of the user's nose; and left and right depressions in the front piece of the framework.

15. The assembly of claim 14, wherein the left and right depressions are molded sections of the front piece of the framework.

16. The assembly of claim 15, wherein the left and right depressions are shaped to rest below an eye of the user when the user wears the assembly.

17. The assembly of claim 16, wherein the left and right depressions allow the user to wear eyeglasses while using the assembly.

18. The assembly of claim 14, wherein the left and right support arms of the framework have a curved posterior portion that are adapted to wrap partially around at least one ears of the user.

19. The assembly of claim 14, wherein each of the plurality of retention clips secures the cannula tube by a compressive force.

20. The assembly of claim 19, wherein the compressive force is created by a difference in the diameter of the interior curvatures of the plurality of retention clips and the outer diameter of the cannula tube.

* * * * *